US00PP12451P2

(12) United States Plant Patent
Utecht

(10) Patent No.: US PP12,451 P2
(45) Date of Patent: Mar. 12, 2002

(54) GERANIUM PLANT NAMED 'FISGREN'

(75) Inventor: Angelika Utecht, Montabaur (DE)

(73) Assignee: Flofis AG, Binningen (CH)

( * ) Notice: Subject to any disclaimer, the term of this patent is extended or adjusted under 35 U.S.C. 154(b) by 0 days.

(21) Appl. No.: 09/772,998

(22) Filed: Jan. 31, 2001

(51) Int. Cl.[7] ..... A01H 5/00
(52) U.S. Cl. ..... Plt./324
(58) Field of Search ..... Plt./324, 325, 330, Plt./328, 332

(56) References Cited

PUBLICATIONS

GTITM UPOVROM Citation for 'Fisgren' as per QZ PBR 991044; Jul. 20, 1999.*
Fischer–Schmülling Plant Alliance Catalog featuring 'FISGREN' on p. 21 (2001).
Official Gazette of the Community Plant Variety Office Oct. 15, 1999; European Union Application, denomination, decision for 'FISGREN'.
German Application for 'FISGREN' Sep. 15, 1998.
German Proposed Denomination for 'FISGREN' Aug. 15, 1999.
Plant Varieties Journal, Jan. 2001, No. 38, p. 66 (Canada).

* cited by examiner

*Primary Examiner*—Bruce R. Campell
*Assistant Examiner*—Kent L. Bell
(74) *Attorney, Agent, or Firm*—Foley & Lardner

(57) ABSTRACT

A new and distinct cultivar of geranium plant named 'Fisgren', as described and illustrated, and particularly characterized by the combined features of bright red, semi-double flowers, numerous medium-sized inflorescences, borne well above the foliage, large, deep green leaves with strong zonation, and vigorous, well-branched growth habit.

1 Drawing Sheet

BACKGROUND OF THE INVENTION

The present invention comprises a new and distinct cultivar of geranium, botanically known as a hybrid of *Pelargonium zonale×peltatum,* and hereinafter referred to by the cultivar name 'Fisgren'. 'Fisgren' originated from a hybridization made by the inventor Angelika Utecht in a controlled breeding program in Hillscheid, Germany, in 1995.

The female parent was a hybrid seedling, no. 92-08-33 (unpatented), of the species *Pelargonium zonale,* having scarlet, semi-double flowers, distinctly zoned foliage, and relatively compact plant habit. The male parent was an ivy geranium (*Pelargonium peltatum*), the hybrid seedling no. 93-125-3 (unpatented), derived from a cross of the commercial (unpatented) varieties 'Hagenbach Rosa', with pink, double flowers, and tall plant habit, and 'Martine', dark-red, single-type flowers. The hybrid seedling was characterized by bright red, single-type flowers, zoned foliage, and vigorous growth. The resulting immature seedlings were grown in tissue culture ("embryo rescue") and finally transferred from the test-tubes into rock-wool cubes and grown in a greenhouse in 1996.

'Fisgren' was selected as one flowering plant within the progeny of the stated cross by Angelika Utecht in a controlled environment in Hillscheid, Germany, in 1996. The first act of asexual reproduction of 'Fisgren' was accomplished when vegetative cuttings were taken from the initial selection in the winter of 1996/1997 in a controlled environment in Galdar, Gran Canaria, Spain, by, or under the supervision of, Angelika Utecht. Horticultural examination of plants grown from the plant initiated in the spring of 1997 in Hillscheid, Germany, and continuing thereafter, has demonstrated that the combination of characteristics as herein disclosed for 'Fisgren' are firmly fixed and are retained through successive generations of asexual reproduction.

'Fisgren' has not been observed under all possible environmental conditions. The phenotype may vary significantly with variations in environment such as temperature, light intensity and day length.

BRIEF DESCRIPTION OF THE INVENTION

The following observations, measurements, and comparisons describe plants grown in Hillscheid, Germany, and in Langley, British Columbia, Canada, under greenhouse conditions which approximate those generally used in commercial practice.

The following traits have been repeatedly observed and are determined to be basic characteristics of 'Fisgren', which in combination distinguish this geranium as a new and distinct cultivar:

1. Bright red, semi-double flowers;
2. Medium-sized, almost semi-spherically shaped inflorescences, well above the foliage;
3. Large, medium-green leaves, with relatively strong zonation;
4. Vigorous growth and well-branched, horizontally spreading plant habit;
5. Medium to late spring flowering response, floriferous throughout the summer; and
6. Robust plant for outdoor planting and tubs/barrels, little care required.

Of the many commercial cultivars known to the present inventor, the most similar in comparison to 'Fisgren' is the variety 'Schöne von Grenchen' (unpatented). In comparison to 'Schöne von Grenchen', 'Fisgren' has a bright red, less orange-red, flower color, more intense green foliage, stronger zonation, and better branched plant habit.

BRIEF DESCRIPTION OF THE DRAWING

The accompanying photographic drawing shows typical flower and foliage characteristics of 'Fisgren' with colors being as true as possible with an illustration of this type. The photograph is a side elevated view of a flowering pot plant. The measurements were taken in Langley, British Columbia, Canada, on Jul. 20, 2000. The plants were growing in 6 inch pots in a greenhouse, and had 15 weeks of cultivation time from the planting of rooted cuttings on Apr. 3, 2000. The plants had not been pinched. In the following description color references are made to The Royal Horticultural Society Colour Chart (R.H.S.). The color values were determined indoors from plants developed in a greenhouse in May, 2000, in Hillscheid, Germany.

Classification:

*Botanical.*—A hybrid between the species *Pelargonium zonale* L'Héritier and *Pelargonium Peltatum* L'Héritier ex Aiton.

*Commercial.*—Hybrid geranium, cv. 'Fisgren'.

Inflorescence:

*Umbel.*—Shape: Nearly semi-spherically. Average diameter: 100 mm. Average depth: 45 mm. Peduncle length: 196 mm. Peduncle: With spur, green, RHS 143 A to 144 A. Pedicel: With spur, 24 mm long.

*Pedicel color, middle part.*—Dark-red to dark violet, from RHS 184 A to RHS 185 B, with occasional green at the base, RHS 143 A. Number of flowers per umbel: About 20 (more than ivy cultivars usually have, less than most zonal varieties). Lastingess of the umbel: Approximately 16–18 days at 18° C.

*Corolla.*—Average diameter: 46 mm. Form: Semi-double. Shape: Zygomorphic, with narrow upper petals. Number of petals: 8–11 per flower. Size of petals: Upper petals are 25–27 mm long, 16–18 mm wide, lower petals are 21–23 mm long, 18–20 mm wide. Shape of upper petals: Spatulate, attenuate base, upper end truncate. Shape of lower petals: Obovate, rounded tip, attenuate base. Color (general tonality from a distance of three meters): Bright red/true red. Color of upper petals: From RHS 44 A to RHS 45 B. Markings of upper petals: Two purple veins, RHS 61 A and a slight fading of color near the bases, stripe between the two veins near the base, from pink, RHS 53 A to purple-pink, RHS 67 C. Color of lower petals: From RHS 44 A to RHS 45 B, no markings. Color of lower surface of petals: Light red, RHS 46 D, with purple pink, RHS 67 C, near the base of upper petals. Number of petaloids: 1–2. Shape of petaloids: No fixed shape, much narrower than petals with filiformis base. Color of petaloids: Upper surface RHS 45 B, lower surface RHS 46 D, base is from white RHS 155 D to bluish-pink RHS 67 D. Color of sepals: Outer surface green, RHS 137 D, inner surface light green, RHS 143 C. Number of sepals: 5. Size of sepals: 12–13 mm in length, 5 mm in width for the largest upper sepal, 3 mm in diameter for the other sepals. Shape of sepals: Linear to lanceolate, acute tip, base truncate, surface with weak, short pubescence, margin entire.

*Bud:* (*immediately prior to unfolding of the petals*).—Shape: Narrow elliptic, slightly asymmetric. Sepal Color (lower part): Green, near RHS 137 D. Petal Color (upper part): Deep red, RHS 45 B. Length: 18 mm. Width: 9 mm.

*Reproductive organs.*—Androecium: 0–2 stamens with white filaments, RHS 155 D, and with an infertile anther, yellow, RHS 19 A. Gynoecium: 5–6 lobed, dull red stigma, whitish style, one pistil per flower. Fertility/Seed set: No seed set observed.

*Spring flowering response period.*—In Hillscheid, Germany, in 2000, plants had on average 1.0 flowers opened 12 weeks after planting of rooted cuttings (pinched plants).

*Outdoor flower production.*—Floriferous in comparison to zonal varieties, and steady flowering throughout the summer; the flower count in Hillscheid, Germany, in 2000, indicated no more than 2–3 inflorescences per plant in mid May, however, as the variety started late, the number of flowers increased thereafter.

*Durability.*—Good shatter resistance, good rain resistance good stability of flower color (little fading, toward RHS 46 C).

*Lastingness of individual bloom.*—Approximately 8 days at 18° C.

*Fragrance.*—None.

Plant:

*Folaige.*—Form: Kidney-shaped, with strong lobes. Base: Open, cordate with open gap between lower lobes. Texture: Slightly glossy, covered with very short pubescence. Margin: Bicrenate, distinctly wavy. Size of leaf: 112 mm wide, approximately 65 mm long. Color of upper surface: Intense green, approximately RHS 137 B. Color of lower surface: RHS 137 D. Zonation: Brown colored, approximately RHS 166 A, strong under outdoor conditions. Size of petioles: 45–55 mm long, 2–3 mm wide. Color of petioles: RHS 143 B.

*General appearance and form.*—Internode length: 20–25 mm. Branching pattern: 6.5 branches. Plant height: 30 week old plant measured from the base of the main stem to the foliage plane is 80–90 cm (slightly trailing like ivy geraniums).

Disease/pest resistance/susceptibility: None observed to date.

I claim:

1. A new and distinct cultivar of geranium plant named 'Fisgren', as described and illustrated.

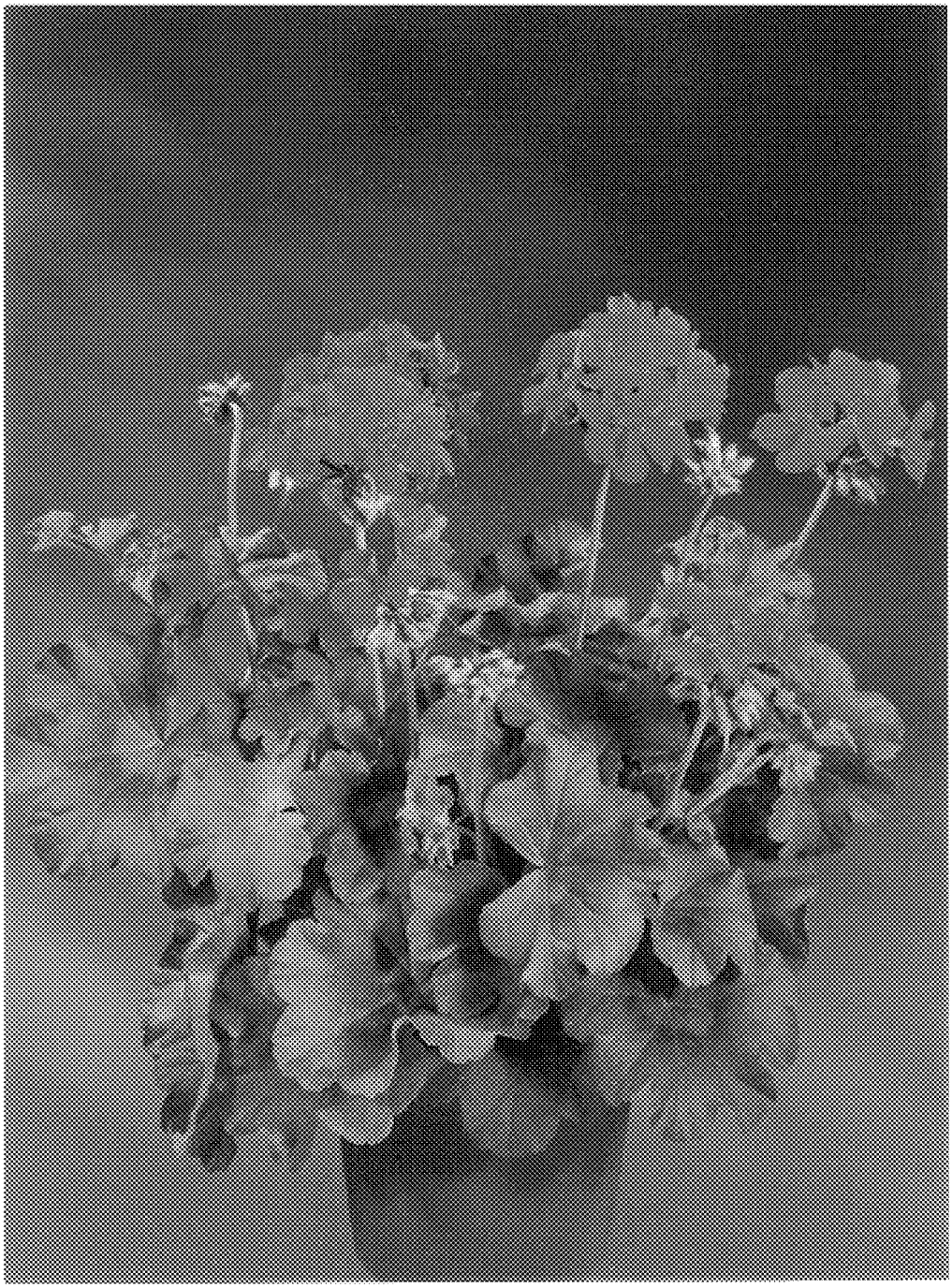

* * * * *